United States Patent [19]
Douglas et al.

[11] Patent Number: 6,121,011
[45] Date of Patent: *Sep. 19, 2000

[54] METHODS FOR APPLYING A REAGENT TO AN ANALYTICAL TEST DEVICE

[75] Inventors: Joel S. Douglas, Los Altos Hills, Calif.; John M. Gleisner, Lynnwood, Wash.

[73] Assignee: Amira Medical, Scotts Valley, Calif.

[ * ] Notice: This patent is subject to a terminal disclaimer.

[21] Appl. No.: 09/205,556

[22] Filed: Dec. 4, 1998

Related U.S. Application Data

[63] Continuation of application No. 09/004,604, Jan. 8, 1998, Pat. No. 5,876,957
[60] Provisional application No. 60/034,668, Jan. 9, 1997.

[51] Int. Cl.[7] .............................. C12Q 1/00; C12Q 1/28; G01N 33/53
[52] U.S. Cl. ................................. 435/28; 435/25; 435/4; 435/283.1; 435/968; 422/50; 422/68.1
[58] Field of Search ................... 435/28, 25, 4, 435/283.1, 968; 422/50, 68.1

[56] References Cited

U.S. PATENT DOCUMENTS

| | | | |
|---|---|---|---|
| 4,130,085 | 12/1978 | Hewitt | 435/28 |
| 4,362,697 | 12/1982 | Tabb et al. | 435/28 |
| 4,848,606 | 7/1989 | Taguchi et al. | 435/28 |
| 4,935,346 | 6/1990 | Phillips et al. | 435/28 |
| 5,306,623 | 4/1994 | Kiser et al. | 435/28 |
| 5,334,247 | 8/1994 | Columbus et al. | 435/28 |
| 5,338,688 | 8/1994 | Rolf et al. | 435/28 |
| 5,529,756 | 6/1996 | Brennan | 435/28 |
| 5,547,702 | 8/1996 | Gleisner | 435/28 |
| 5,876,957 | 3/1999 | Douglas et al. | 435/28 |

FOREIGN PATENT DOCUMENTS 0620437  10/1994  European Pat. Off. .

*Primary Examiner*—Louise N. Leary
*Attorney, Agent, or Firm*—Burns, Doane, Swecker & Mathis, LLP

[57] ABSTRACT

This invention provides methods and apparatus for applying a reagent to an analytical test device. The methods and apparatus employ a nozzle and a flexible restrictor to accurate control the amount of reagent applied to the test device. The analytical test devices prepared by the methods of this invention are used to determine the presence or the quantity of an analyte in a liquid sample, such as whole blood.

19 Claims, 4 Drawing Sheets

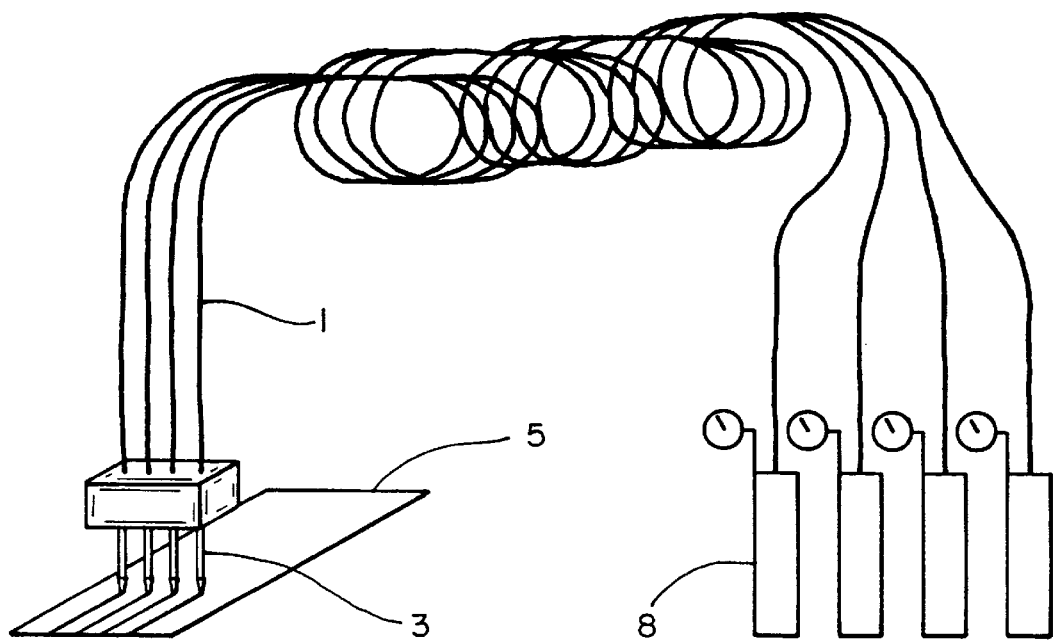
FIG_1
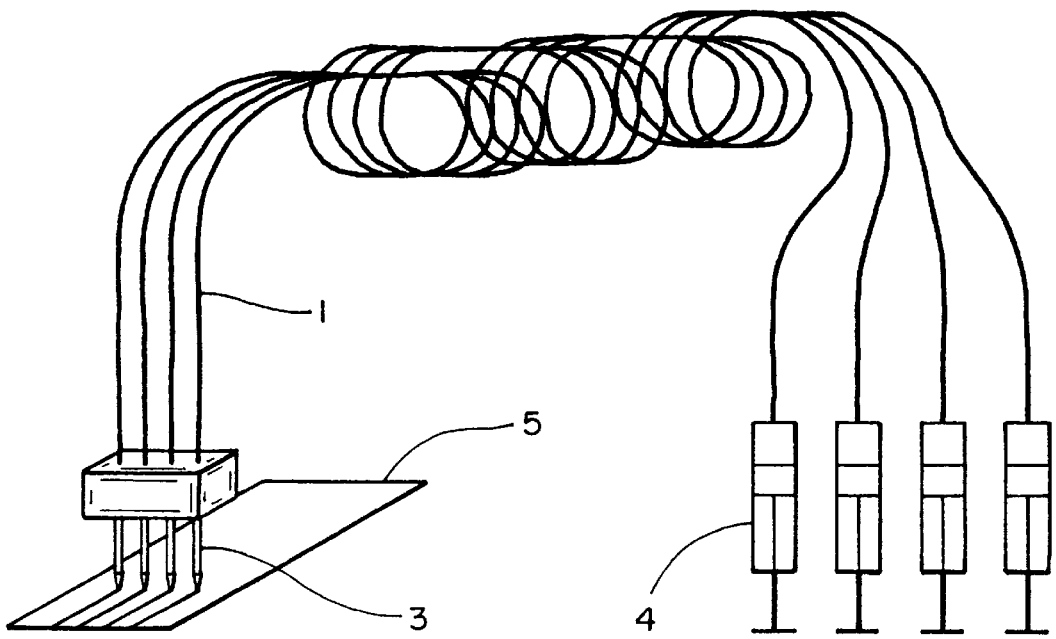
FIG_2

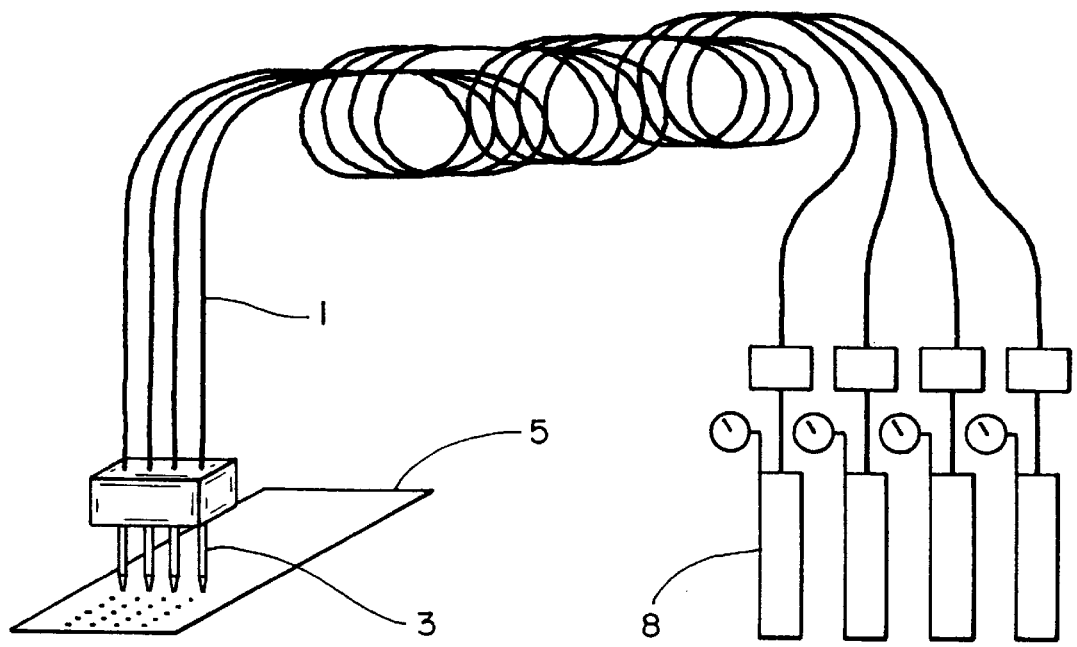
FIG_3
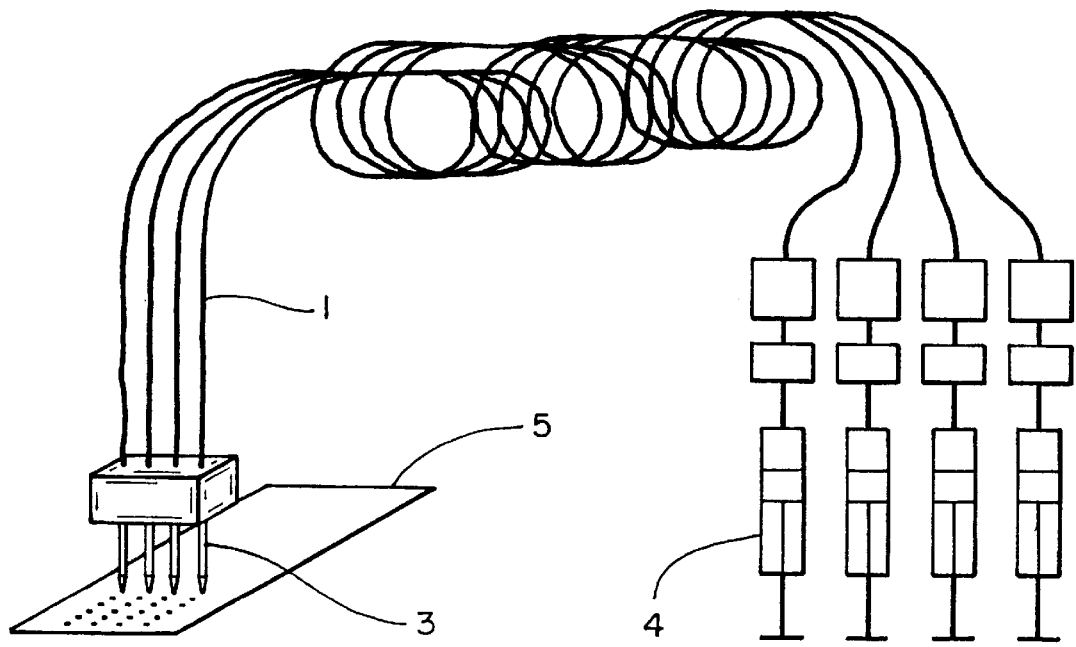
FIG_4

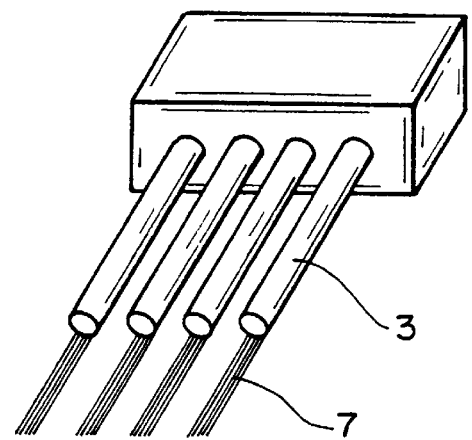
FIG_5
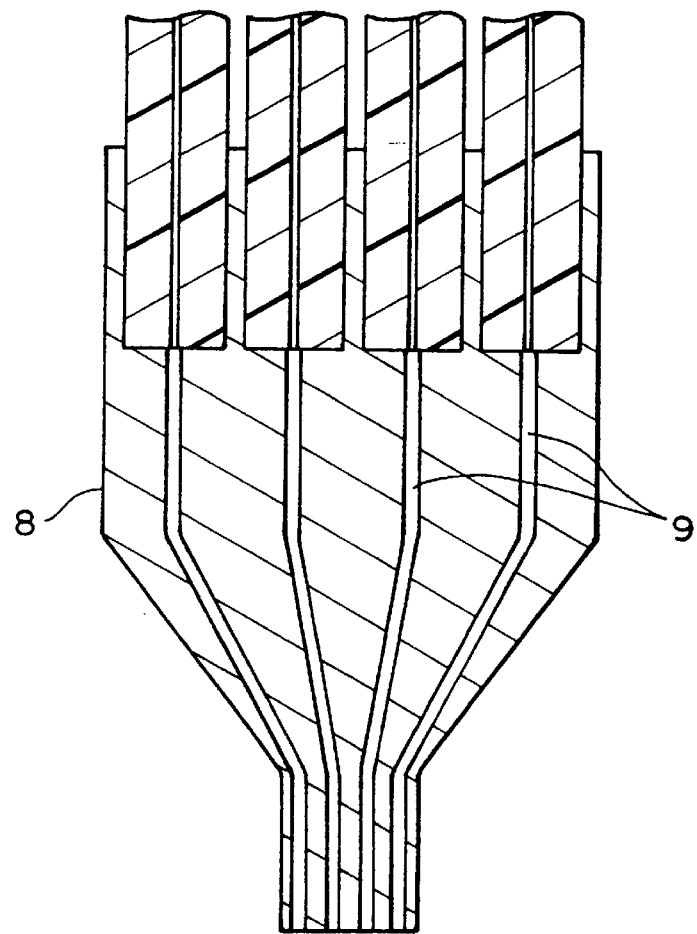
FIG_6

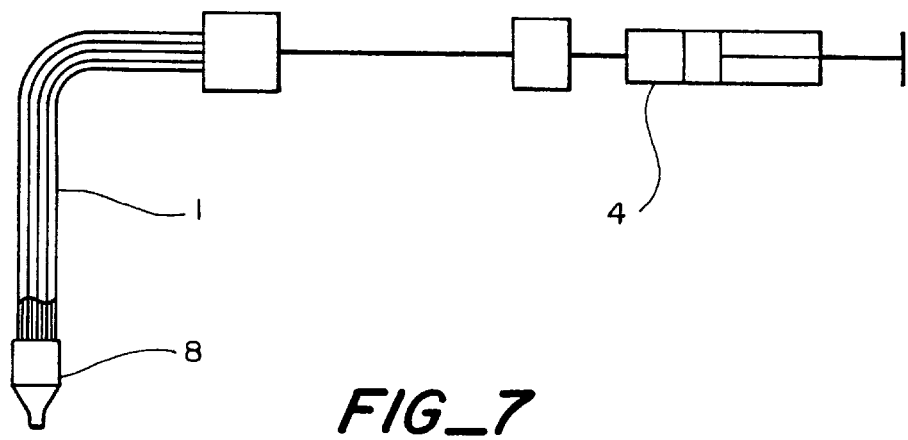
FIG_7
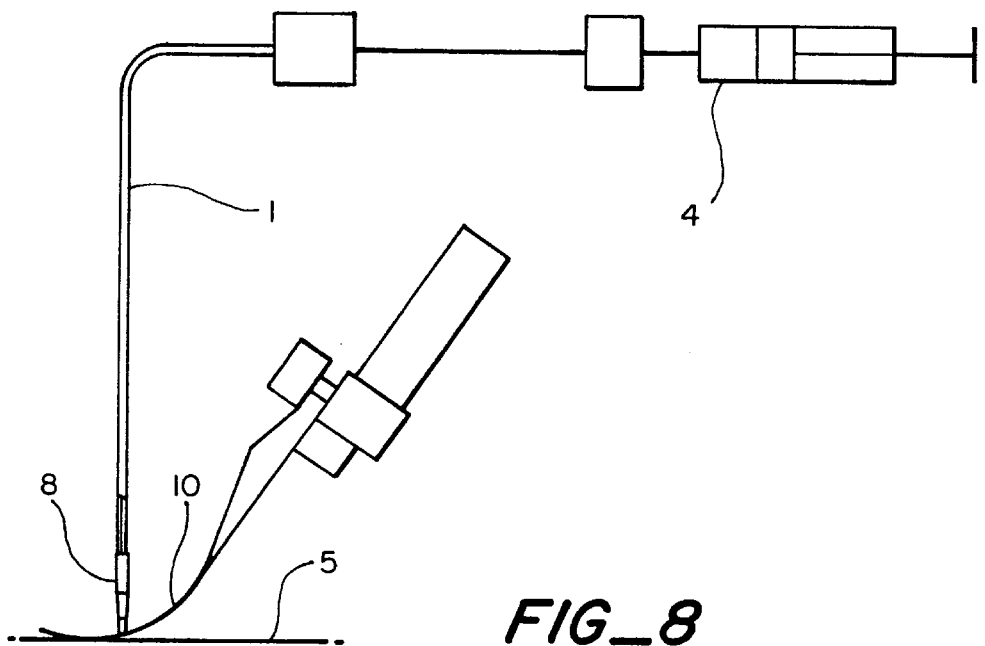
FIG_8

METHODS FOR APPLYING A REAGENT TO AN ANALYTICAL TEST DEVICE

CROSS-REFERENCE TO RELATED APPLICATIONS

This application is a continuation of application Ser. No. 09/004,604, filed Jan. 8, 1998, now U.S. Pat. No. 5,876,957.

This application claims the benefit of U.S. Provisional Application No. 60/034,668, filed Jan. 9, 1997, which application is incorporated herein in its entirety.

BACKGROUND OF THE INVENTION

1. Field of Invention

This invention relates to improved methods for applying a reagent to an analytical test device. The test devices prepared by the methods of this invention are typically used to determine the presence and/or the quantity of an analyte in a liquid test sample, such as whole blood. This invention also provides apparatus for applying the reagent to the analytical test device.

2. State of the Art

Analytical test devices containing a reagent are commonly used to determine the presence or the quantity of a particular analyte in liquid samples, such as whole blood. For example, diabetics typically use such test devices to monitor the level of glucose in their blood. The reagent on the test device typically indicates the presence or the quantity of the analyte in the liquid sample using either spectrophotographic, color match or electrochemical technology. Such test devices generally comprise a substrate, such as a non-porous handle, and an absorbent test pad attached to the handle. The reagent is typically applied to the test pad either before or after assembly and then dried to create a "dry" chemical test device.

Numerous methods of applying reagents and coatings to analytical test devices have been described in the literature. These methods include dip coating, roll coating, ink jet application, screen printing, brushing, painting and the like.

For example, Bertek, Inc. literature entitled "The Technology of Coating and Laminating" (1986) describes various coating technologies and techniques, including roll coating, knife over roll and slot coating methods. These methods typically apply the reagents either across the whole web of the test device or in a continuous manner.

Similarly, U.S. Pat. No. 5,547,702 to Gleisner, describes a method of applying a reagent mixture down a reagent test pad in a continuous manner.

Many other patents describe imbibing processes such as dip coating processes. For example, U.S. Pat. No. 4,935,346 to Phillips et al., describes a process in which a membrane is dip coated and then dried.

When the test devices prepared by such methods are used to determine the quantity of an analyte in a liquid sample, it is particularly important that the amount of reagent deposited on the test device be accurately controlled so that reproducible test results are achieved. Additionally, the reagents employed in the test devices are often expensive and need to be conserved. Therefore, it is particularly important that the reagent be applied to the test device only where it is needed. Accordingly, it would highly desirable to develop novel methods and apparatus for applying the reagent to the test device such the reagent is deposited on the test device in an accurate and controlled manner.

SUMMARY OF THE INVENTION

The present invention provides improved methods and apparatus for applying a reagent to an analytical test device. The methods and apparatus of this invention employ flexible restrictors to accurately control the amount of reagent applied to the test device. Such restrictors allow the reagent to be applied to the test device in a predetermined amount thereby providing reproducible test results. Applying the reagent with such restrictors also allows the reagent to be applied only where it is needed thus conserving expensive reagents.

Accordingly, in one of its method aspects, the present invention provides a method for applying a reagent to a test device comprising:

(a) providing a test device comprising a substrate and a test pad attached to the substrate;

(b) providing a fluid delivery system comprising a nozzle and a flexible restrictor attached to the nozzle for delivery of a reagent from the nozzle to the test pad;

(c) applying a reagent comprising an indicator system and an oxidase enzyme or a peroxidase enzyme in a predetermined amount and at a predetermined pressure through the nozzle and the flexible restrictor to the test pad.

In a preferred embodiment of this invention, the fluid delivery system further comprises a pressure delivery system. The pressure delivery system feeds the reagent into the flexible restrictor in a controlled manner for application to the test pad through the nozzle.

In another preferred embodiment, the fluid delivery system further comprises a positive displacement system. The positive displacement system feeds the reagent into the flexible restrictor in a controlled manner for application to the test pad through the nozzle.

In still another preferred embodiment, a brush is attached to the underside of the nozzle and the reagent is applied through the nozzle and then through the brush to the test pad. In this embodiment, the brush applies or paints the reagent onto the test pad. In addition to applying the reagent more evenly on the test pad, the brushes also provide additional damping of any pulsation from the pumping system.

The reagent can be applied to the test pad continuously or in a discrete amount. Accordingly, in a preferred embodiment of this invention, the reagent is applied to the test pad in a metered amount continuously down the length of the pad. When the reagent is applied continuously to the test pad, the nozzle preferably has an internal diameter ranging from about 0.005 to about 0.150 inches and a length ranging from about 0.2 to about 2.0 inches. Additionally, when applied in this manner, the flexible restrictor preferably has an internal diameter ranging from about 0.002 to about 0.200 inches and a length of about 0.5 to about 12 feet.

In another preferred embodiment, the reagent is applied to the test pad in an discrete amount to the reaction area of the pad. When applied in this manner, the nozzle has an internal diameter which is less than or equal to 0.032 inches and a length ranging from about 0.2 to about 2.0 inches. Preferably, in this embodiment, the flexible restrictor has an internal diameter ranging from about 0.002 to about 0.200 inches and a length of about 0.5 to about 12 feet.

Preferably, the oxidase enzyme employed in the test strip is selected from the group consisting of glucose oxidase, cholesterol oxidase, uricase, alcohol oxidase, aldehyde oxidase and glycerophosphate oxidase. More preferably, the oxidase enzyme is glucose oxidase.

The indicator system employed in this invention is preferably selected from the group consisting of (a) 3-methyl-2-benzothiazolinone hydrazone hydrochloride and 3-dimethylaminobenzoic acid; (b) 3-methyl-2-benzothiazolinone hydrazone hydrochloride and 3,5- dichloro-2-hydroxybenzenesulfonic acid; (c) 4-aminoantipyrene and 5-oxo-1-(p-sulfophenyl)-2-pyrazoline-3-carboxylic acid; (d) 4-aminoantipyrene and N-(m-tolyl)-diethanolamine; (e) 4-aminoantipyrene and 4-methoxynaphthol; (f) 2,2'-azino-di-(3-ethylbenzthiazoline)sulfonic acid; (g) pyrogallol red; (h) bromopyrogallol red; (i) acid green 25; (j) 3-methyl-2-benzothiazolinone hydrazone hydrochloride and 8-anilino-1-naphthalenesulfonate; (k) 3-methyl-2-benzothiazolinone hydrazone hydrochloride and N-(3-sulfopropyl)aniline; (l) 3-methyl-6-(sulfonate)-benzothiazolinone-(2)-hydrazone sodium salt and 3-dimethylaminobenzoic acid; (m) 3-methyl-6-(sulfonate)-benzothiazolinone-(2)-hydrazone sodium salt and 8-anilino-1-naphthalenesulfonate; and (n) 3-methyl-6-(sulfonate)-benzothiazolinone-(2)-hydrazone sodium salt and N-(3-sulfopropyl)aniline.

Using the methods of this invention, the reagent can be applied to multiple tracks of test pad thereby increasing the throughput of the system. Alternatively, the methods of this invention can be employed to apply or lay down different concentrations of reagent on isolated test pads.

In one preferred embodiment, the fluid delivery system comprises a plurality of nozzles and flexible restrictors. Preferably, the multiple nozzle are joined together to form a slotted-head applicator. If desired, each of the plurality of nozzles and flexible restrictors can apply a different concentration of reagent to the test pad thereby creating a gradient effect between each application of reagent. Alternatively, each nozzle and flexible restrictor can be used to apply a different reagent to the test pad.

In another of its aspects, the present invention provides an apparatus for applying a reagent to a test device comprising a substrate and a test pad, said apparatus comprising:

(a) a fluid delivery system comprising a nozzle and a flexible restrictor for delivery of the reagent to the test pad;

(b) a support positioned under the fluid delivery system for supporting the test device; and (c) means for moving the test device under the fluid delivery system.

In a preferred embodiment, the fluid delivery system of the apparatus further comprises a pressure delivery system. The pressure delivery system feeds the reagent into the flexible restrictor in a controlled manner for application to the test pad through the nozzle.

In another preferred embodiment, the fluid delivery system of the apparatus further comprises a positive displacement system. The positive displacement system feeds the reagent into the flexible restrictor in a controlled manner for application to the test pad through the nozzle.

In still another preferred embodiment, a brush (such as a felt pad) is attached to the underside of the nozzle and the reagent is applied through the nozzle and then through the brush to the test pad.

In a preferred embodiment, the nozzle employed in the apparatus has an internal diameter ranging from about 0.005 to about 0.150 inches and a length ranging from about 0.2 to about 2.0 inches. In this embodiment, the flexible restrictor preferably has an internal diameter ranging from about 0.002 to about 0.200 inches and a length of about 0.5 to about 12 feet. This embodiment of the apparatus is particularly preferred for applying the reagent in a continuous manner.

In another preferred embodiment, the nozzle employed in the apparatus has an internal diameter which is less than or equal to 0.032 inches and a length ranging from about 0.2 to about 2.0 inches. In this embodiment, the flexible restrictor has an internal diameter ranging from about 0.002 to about 0.200 inches and a length of about 0.5 to about 12 feet. This embodiment of the apparatus is particularly preferred for applying discrete amounts of the reagent to the test pad.

In a preferred embodiment of the apparatus, the means for moving the test device is a conveyor.

In another preferred embodiment, the fluid delivery system comprises a plurality of nozzles and flexible restrictors. Preferably, the each of the plurality of nozzles and flexible restrictors is employed to apply a different concentration of the reagent thereby creating a gradient effect between each application of reagent.

BRIEF DESCRIPTION OF THE DRAWINGS

FIG. 1 is a view of a continuous multi-nozzle coating system using a long flexible restrictor and a pressure delivery system.

FIG. 2 is a view of a continuous multi-nozzle coating system using a long flexible restrictor and a positive displacement delivery system.

FIG. 3 is a view of a discrete multi-nozzle coating system using a long flexible restrictor and a pressure delivery system.

FIG. 4 is a view of a discrete multi-nozzle coating system using a long flexible restrictor and a positive displacement delivery system.

FIG. 5 is a view of a nozzle system with brushes to dampen pump pulsation.

FIG. 6 is a view of a slotted-head multiple nozzle.

FIG. 7 is a view of a slotted-head multiple nozzle coating system using a long flexible restrictors and a pressure delivery system.

FIG. 8 is a view of a slotted-head multiple nozzle with a brush (felt pad) attached.

DETAIL DESCRIPTION OF THE INVENTION

Test devices made using the methods and fluid delivery systems of the present invention to imbibe the reagent into the test pad use complete or partial prefabricated test devices. The test devices move either on a conveyor suitable for moving the test devices or as a continuous web. The amount of fluid required and the coverage is calculated so that the appropriate volume of reagent is dispensed on the device test pad.

For continuous deposition, the fluid delivery system dispenses a continuous stream of reagent. The length of the restrictor, the size of the nozzle, and the system pressure are selected using an iterative process to determine the amount of reagent delivered. The amount of fluid delivered is directly linked to the internal diameter (id) of the restrictor and nozzle and the length of each. For volumes in the range of less than one milliliter per minute, the nozzle id preferably ranges from about 0.005 to about 0.150 inches (about 0.0127 to about 0.381 cm) and has a length of about 0.2 to about 2.0 inches (about 0.51 to about 5.1 cm). To minimize any pulsation in the system, the restrictors preferably have an id of from 0.002 to 0.200 inches (about 0.011 to about 0.51 cm) and a length of about 0.5 to 12 feet (about 0.152 to about 3.66 m) depending on the temperature of the surrounding environment. Preferably, the restrictors are made from a flexible tubing, such as nylon or tygon. This creates a slight accumulation capacity in the system to damp out any pulsation. The nozzle size for this example would have an id of 0.015 inches and a length of 6 inches. The composition of the nozzle is preferably PVC plastic, stainless steel or glass.

For discrete deposition, the invention generally dispenses a predetermined amount of reagent, typically in the form of a drop. The length of the restrictor, the size of the nozzle and system pressure are selected using a similar iterative process as described above. However, to determine nozzle length and size, the amount to be delivered to an application site must be determined and the nozzles selected with a suitable end which can support formation of an adequate drop. The amount of fluid delivered is directly linked to the nozzle tip dimensions and shape, and to the internal diameter (id) of the restrictor and nozzle and the length of each. For volumes in the range of less than one milliliter per minute, the nozzle id is preferably less than or equal to 0.032 inches (0.0813 cm) and the length is preferably about 0.2 to about 2.0 inches (about 0.51 to about 5.1 cm). The restrictors preferably have an id of from 0.002 to about 0.200 inches (about 0.011 to about 0.51 cm) and a length of about 0.5 to about 12 feet (about 0.152 to about 3.66 m) depending on the temperature of the surrounding environment. To minimize any pulsation in the system, the restrictors are preferably made from a flexible tube such as nylon or tygon. This creates a slight accumulation capacity in the system to damp out any pulsation. The nozzle size for this example would have an id of 0.015 inches and a length of 6 inches. The composition of the nozzle is preferably PVC plastic, stainless steel or glass.

The opening of the nozzles employed in this invention may have any art-recognized shape, including round, oval or slit nozzles. The nozzle shape will typically be chosen based on the amount and the surface area of reagent desired on the test pad.

The fluid delivery system in either case typically further comprises a positive displacement system or pressure system. Examples of positive displacement systems include gravity feed systems and the like. Pressure systems include syringes, continuous flow pumps and the like. Pressure delivery systems for discrete reagent application require very fine pressure control and sharp on/off switching capabilities. A system such as those built by EFD corporation of Providence, R.I. (Model 1000DV) is suitable for use in this invention. Syringe pumps made by ISCO pump or Harvard Apparatus can also accommodate the deliver requirements for low volume discrete deliver applications.

Pumps create pulsations due to sticking of the seals or peristaltic action. If the flexible restrictors and nozzles are not sufficient to dampen these pulsation, a brush is preferably used on the underside to provide a path for the reagent to the membrane. The term brush refers to any object which serves to spread the reagent on the surface of the pad, including brushes with bristles and other spreading objects such as felt pads and the like.

In one of its embodiments, the present invention employs a plurality of nozzles and flexible restrictors. In this embodiment, the nozzles can be joined together to form a slotted-head. The various nozzles and flexible restrictors allow different concentrations of the reagent to be applied to the test pad. This creates a concentration gradient across the test pad. Alternatively, different reagents can be applied through each of the nozzles The reagent system used in this invention must be capable of detecting the presence of the analyte. In general, the analyte reacts with a specific oxidase or peroxidase enzyme and produces hydrogen peroxide. This strongly oxidative substance reacts with the indicator(s) present to produce a colored end product. Preferred oxidase enzymes for use in this invention include, but are not limited to, the following: glucose oxidase, cholesterol oxidase, uricase, alcohol oxidase, aldehyde oxidase or glycerophosphate oxidase. Other oxidase or peroxidase enzymes will be readily evident to one who is skilled in the art.

The indicator chemistries which provide acceptable color generation when applied to the test pad may be chosen from 3-methyl-2-benzothiazolinone hydrazone hydrochloride (MBTH) combined with 3-dimethylaminobenzoic acid (DMAB), MBTH combined with 3,5-dichloro-2-hydroxybenzene-sulfonic acid (DCHBS); 4-aminoantipyrene (4-AAP) and 5-oxo-1-(p-sulfophenyl)-2-pyrazoline-3-carboxylic acid (OPSP); 4-AAP and N-(m-tolyl)-diethanolamine (NDA); 2,2'-azino-di-(3-ethylbenzthiazoline)sulfonic acid (ABTS); 4-AAP and 4-methoxynaphthol; pyrogallol red (PGR); bromopyrogallol red (BPR); acid green 25 (AG); MBTH and 8-anilino-1-naphthalenesulfonate (ANS); or N-(3-sulfopropyl)aniline and MBTH; or other known and conventional dye system for different analytes. U.S. Pat. No. 5,306,623 to Kiser et. al. discloses effective concentrations of a number of useful dye systems. Many other indicator reagent systems are known in the art and any of these may be used in this invention.

A preferred dye system is based on the sulfonated form of MBTH, 3-methyl-6-(M sulfonate)-benzothiazolinone-(2)-hydrazone (MBTH-S) where M is sodium, potassium, ammonium or other equivalent ion, but is preferably sodium. Sulfonation of MBTH to form MBTH-S is disclosed in U.S. Pat. No. 4,101,381 to Klose. MBTH-S formed as a dye couple with DMAB, ANS or N-(3-sulfopropyl)aniline provides preferred indicator systems having stable color end points in a short period of time.

The particular reagent system employed in this invention will determine, in part, the id and length of the nozzle and the restrictor employed. Typically, a smaller id and/or a longer length for the nozzle and/or the restrictor will be used when the reagent has a lower viscosity. Alternatively, the viscosity of the reagent can be modified or optimized for a particular delivery system by the addition to the reagent of well-known viscosity modifying agents and/or by controlling the temperature of the reagent. In the latter case, the reagent can be warmed or cooled by heating or cooling the restrictors and/or the reagent reservoirs. For example, the restrictors and reagents reservoirs can be cooled to the desired temperature by immersing the restrictors and reservoirs in an ice bath or by surrounding them with a refrigeration system. Similiarly, heating may be accomplished using a warm water bath or an oven. Depending on the reagent, cooling of the restrictors and reagent reservoirs also has the additional benefit of stabilizing the reagent system thereby preventing or reducing the decomposition of the reagent. Accordingly, the length of time the reagent is useable may be significantly increased.

A further description of this invention may be obtained from the drawings.

FIG. 1 is a view of a continuous multi-nozzle coating system using a long flexible restrictor 1 and a pressure pot delivery system 8 and nozzle 3. The reagent is dispensed from the nozzle and test pad 5 is impregnated.

FIG. 2 is a view of a continuous multi-nozzle coating system using a long flexible restrictor 1 and a positive displacement delivery system 4 and nozzles 3. The reagent is dispensed from the nozzle and test pad 5 is impregnated.

FIG. 3 is a view of a discrete multi-nozzle coating system using a long flexible restrictor 1 and a pressure delivery system 8 and nozzles 3. The reagent is dispensed from the nozzle and test pad 5 is impregnated.

FIG. 4 is a view of a discrete multi-nozzle coating system using a long flexible restrictor 1 and a positive displacement delivery system 4 and nozzles 3. The reagent is dispensed from the nozzle and test pad 5 is impregnated.

FIG. 5 is a view of a nozzle system with nozzle 3 and brushes 7 to dampen pump pulsation and provide flow control. If the flexible restrictors and nozzles are not sufficient to dampen these pulsation, a brush is used on the underside to provide a path for the reagent to the membrane.

FIG. 6 is a view of a multiple slotted-head nozzle 8 having multiple openings 9 for delivery of multiple reagents or different concentrations of reagents to a test pad.

FIG. 7 is a view of a multiple slotted-head nozzle coating system using long flexible restrictors 1 and a pressure delivery system 4 and a multiple slotted-head nozzle 8. The reagent is dispensed from the nozzle to the test pad.

FIG. 8 is a view of a multiple slotted-head nozzle coating system using long flexible restrictors 1 and a pressure delivery system 4 and a multiple slotted-head nozzle 8 having a felt pad 10 attached. The reagent is dispensed from the nozzle through the felt pad to the test pad 5.

What is claimed is:

1. A method for applying a reagent to a test device comprising:
    (a) providing a test device comprising a substrate and a test pad attached to the substrate;
    (b) providing a fluid delivery system comprising a nozzle and a flexible restrictor attached to the nozzle for delivery of a reagent from the nozzle to the test pad;
    (c) applying a reagent comprising an indicator system and glucose oxidase in a predetermined amount and at a predetermined pressure through the nozzle and the flexible restrictor to the test pad, wherein the indicator system comprises 3-methyl-6-(M sulfonate)-benzothiazolinone-(2)-hydrazone where M is sodium, potassium or ammonium and a second dye component capable of forming a dye couple with 3-methyl-6-(M sulfonate)-benzothiazolinone-(2)-hydrazone.

2. The method of claim 1 wherein the fluid delivery system further comprises a pressure delivery system.

3. The method of claim 1 wherein the fluid delivery system further comprises a positive displacement system.

4. The method of claim 1 wherein a brush is attached to the underside of the nozzle and the reagent is applied through the nozzle and then through the brush to the test pad.

5. The method of claim 1 wherein the reagent is applied continuously to the test pad.

6. The method of claim 5 wherein the nozzle has an internal diameter ranging from about 0.005 to about 0.150 inches and a length ranging from about 0.2 to about 2.0 inches, and the flexible restrictor has an internal diameter ranging from about 0.002 to about 0.200 inches and a length of about 0.5 to about 12 feet.

7. The method of claim 1 wherein the reagent is applied in a discrete amount to the test pad.

8. The method of claim 7 wherein the nozzle has an internal diameter which is less than or equal to 0.032 inches and a length ranging from about 0.2 to about 2.0 inches, and the flexible restrictor has an internal diameter ranging from about 0.002 to about 0.200 inches and a length of about 0.5 to about 12 feet.

9. The method of claim 1 wherein the indicator system is selected from the group consisting of 3-methyl-6-(sulfonate)-benzothiazolinone-(2)-hydrazone sodium salt and 3-dimethylaminobenzoic acid; 3-methyl-6-(sulfonate)-benzothiazolinone-(2)-hydrazone sodium salt and 8-anilino-1-naphthalenesulfonate; and 3-methyl-6-(sulfonate)-benzothiazolinone-(2)-hydrazone sodium salt and N-(3-sulfopropyl)aniline.

10. The method of claim 1 wherein the fluid delivery system comprises a plurality of nozzles and flexible restrictors.

11. The method of claim 10 wherein each of the plurality of nozzles and flexible restrictors applies a different concentration of reagent to the test pad.

12. An apparatus for applying a reagent to a test device comprising a substrate and a test pad, said apparatus comprising:
    (a) a fluid delivery system comprising a nozzle and a flexible restrictor for delivery of the reagent to the test pad;
    (b) a support positioned under the fluid delivery system for supporting the test device; and
    (c) means for moving the test device under the fluid delivery system;
    wherein the reagent comprises an indicator system and glucose oxidase and further wherein the indicator system comprises 3-methyl-6-(M sulfonate)-benzothiazolinone-(2)-hydrazone where M is sodium, potassium or ammonium and a second dye component capable of forming a dye couple with 3-methyl-6-(M sulfonate)-benzothiazolinone-(2)-hydrazone.

13. The apparatus of claim 12 wherein the fluid delivery system further comprises a pressure delivery system.

14. The apparatus of claim 12 wherein the fluid delivery system further comprises a positive displacement system.

15. The apparatus of claim 12 wherein a brush is attached to the underside of the nozzle and the reagent is applied through the nozzle and then through the brush to the test pad.

16. The apparatus of claim 12 wherein the nozzle has an internal diameter ranging from about 0.005 to about 0.150 inches and a length ranging from about 0.2 to about 2.0 inches, and the flexible restrictor has an internal diameter ranging from about 0.002 to about 0.200 inches and a length of about 0.5 to about 12 feet.

17. The apparatus of claim 12 wherein the nozzle has an internal diameter which is less than or equal to 0.032 inches and a length ranging from about 0.2 to about 2.0 inches, and the flexible restrictor has an internal diameter ranging from about 0.002 to about 0.200 inches and a length of about 0.5 to about 12 feet.

18. The apparatus of claim 12 wherein the means for moving the test device is a conveyor.

19. The apparatus of claim 12 wherein the fluid delivery system comprises a plurality of nozzles and flexible restrictors.

* * * * *